US009844532B2

(12) United States Patent
Lai et al.

(10) Patent No.: US 9,844,532 B2
(45) Date of Patent: Dec. 19, 2017

(54) INFANT NUTRITIONAL PRODUCT WITH RRR ALPHA-TOCOPHEROL

(71) Applicant: ABBOTT LABORATORIES, Abbott Park, IL (US)

(72) Inventors: Chron-Si Lai, Blacklick, OH (US); Matthew Kuchan, Westerville, OH (US); Gary Katz, Columbus, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 14/774,889

(22) PCT Filed: Mar. 13, 2014

(86) PCT No.: PCT/US2014/026339
§ 371 (c)(1),
(2) Date: Sep. 11, 2015

(87) PCT Pub. No.: WO2014/160335
PCT Pub. Date: Oct. 2, 2014

(65) Prior Publication Data
US 2016/0022628 A1    Jan. 28, 2016

Related U.S. Application Data

(60) Provisional application No. 61/778,653, filed on Mar. 13, 2013.

(51) Int. Cl.
| | | |
|---|---|---|
| *A61K 31/355* | (2006.01) | |
| *A61K 31/202* | (2006.01) | |
| *A61K 31/05* | (2006.01) | |
| *A61K 31/375* | (2006.01) | |
| *A23L 33/00* | (2016.01) | |
| *A23L 33/12* | (2016.01) | |
| *A23L 33/15* | (2016.01) | |

(52) U.S. Cl.
CPC ............ *A61K 31/355* (2013.01); *A23L 33/12* (2016.08); *A23L 33/15* (2016.08); *A23L 33/40* (2016.08); *A61K 31/05* (2013.01); *A61K 31/202* (2013.01); *A61K 31/375* (2013.01); *A23V 2002/00* (2013.01); *A23V 2200/00* (2013.01)

(58) Field of Classification Search
None
See application file for complete search history.

(56) References Cited

U.S. PATENT DOCUMENTS

| | | | |
|---|---|---|---|
| 5,492,899 | A | 2/1996 | Masor et al. |
| 7,090,879 | B2 | 8/2006 | Albrecht et al. |
| 7,829,126 | B2 | 11/2010 | Barrett-Reis et al. |
| 2003/0104078 | A1 | 6/2003 | Barrett-Reis et al. |
| 2004/0202765 | A1 | 10/2004 | McMahon et al. |
| 2005/0208179 | A1 | 9/2005 | Albrecht et al. |
| 2006/0171993 | A1* | 8/2006 | Barrett-Reis ........ A61K 31/355 424/439 |
| 2006/0205826 | A1 | 9/2006 | Romero et al. |
| 2007/0098849 | A1 | 5/2007 | Barrett-Reis et al. |
| 2008/0003330 | A1 | 1/2008 | Rueda et al. |
| 2011/0213039 | A1 | 9/2011 | Barrett-Reis et al. |
| 2014/0010912 | A1 | 1/2014 | Clinger et al. |
| 2015/0025133 | A1 | 1/2015 | Lai et al. |
| 2016/0008318 | A1 | 1/2016 | Lai |

FOREIGN PATENT DOCUMENTS

| | | |
|---|---|---|
| CA | 2802910 | 12/2011 |
| CN | 1397178 | 2/2003 |
| CN | 1792194 | 6/2006 |
| CN | 101856046 | 10/2010 |
| CN | 102132742 | 7/2011 |
| WO | 03017945 | 3/2003 |
| WO | 2005054415 | 6/2005 |
| WO | 2007050521 | 5/2007 |
| WO | 2008103370 | 8/2008 |
| WO | 2010112429 | 10/2010 |
| WO | 2012092085 | 7/2012 |
| WO | 2013101494 | 7/2013 |
| WO | 2013138157 | 9/2013 |
| WO | 2014159967 | 10/2014 |

OTHER PUBLICATIONS https://dietarysupplementdatabase.usda.nih.gov/conversions.html referenced on May 19, 2017.*
International Search Report and Written Opinion for PCT/US2014/025541 dated Jun. 20, 2014.
International Preliminary Report on Patentability for PCT/US2014/025541 dated Sep. 15, 2015.
International Search Report and Written Opinion for PCT/US2014/026339 dated Jun. 20, 2014.
International Preliminary Report on Patentability for PCT/US2014/026339 dated Sep. 15, 2015.
Office Action in U.S. Appl. No. 14/771,719 dated Sep. 9, 2016.
Office Action in CN Application No. 201480026211.0 dated Sep. 9, 2016.
Rules 161(1) and 162 Communication in EP Application No. 14716172.3 dated Oct. 21, 2015.
Rules 161(1) and 162 Communication in EP Application No. 14716161.6 dated Nov. 5, 2015.

(Continued)

*Primary Examiner* — Jessica Worsham
(74) *Attorney, Agent, or Firm* — Calfee, Halter & Griswold LLP

(57) ABSTRACT

This invention relates to a method of improving CNS maturation in an infant by administering a mixture of natural tocopherols, wherein the composition contains an optimum tocopherol profile similar to that found in human breast milk, and can encompass a tocopherol profile from early stage to transitional to mature human breast milk. For ease of administration and maximized efficacy, the optimized mixture of natural tocopherols are typically delivered in an oral dosage form with a limited level of non-RRR alpha-tocopherols to maximize efficacy of the RRR alpha-tocopherol on stimulating post-natal CNS development.

16 Claims, No Drawings

(56) References Cited

OTHER PUBLICATIONS

Acuff et al., "Relative bioavailability of RRR-and all-rac-a-tocopheryl acetate in humans: studies using deuterated compounds 3," American Society for Clinical Nutrition, Jan. 1, 1994, pp. 397-402.

Gill et al., Liquid chromatographic method for the determination of lutein in milk and pediatric formulas, International Dairy Journal, vol. 18, Issue 9, Sep. 2008, pp. 894-898.

Holman et al., "Deficiency of essential fatty acids and membrane fluidity during pregnancy and lactation," Proceedings of the National Academy of Sciences of the United States of America, vol. 88, No. 11, Jun. 1, 1991, pp. 4835-4839.

Rubin et al., Effect of carotenoid supplementation on plasma carotenoids, inflammation and visual development in preterm infants, J. of Perinatology, (Jun. 2012), 32(6), pp. 418-424.

Office Action in CA 2,903,703 dated Nov. 8, 2016.
Communication Pursuant to Article 94(3) in EP Application No. 14716172.3 dated Dec. 15, 2016.
Search Report in SG 11201507210X dated Jul. 29, 2016.
Written Opinion in SG 11201507210X dated Nov. 9, 2016.
Bettler, J. et al., Serum lutein concentrations in healthy term infants fed human milk or infant formula with lutein. European Journal of Nutrition, 2010, vol. 49, pp. 45-51.
Gualtieri, C.T. Cognitive Enhancers and Neuroprotectants. In Brain Injury and Mental Retardation (Chapter 25); Lippincott Williams & Wilkins; Philadelphia, PA (2004).
Lebold, K. M., "Embryogenesis is dependent upon 12-lipoxygenase, 5-lipoxygenase, and α-tocopherol to modulate polyunsaturated fatty acid status and the production of oxidized fatty acids in zebrafish," Master of Science Thesis, Oregon State University, May 25, 2012.

* cited by examiner

INFANT NUTRITIONAL PRODUCT WITH RRR ALPHA-TOCOPHEROL

CROSS REFERENCE TO RELATED APPLICATIONS

This application is the U.S. national stage entry of International Application No. PCT/US2014/026339,filed March 13, 2014,which claims priority to and any benefit of U.S. Provisional Application No. 61/778,653,filed March 13, 2013,the entire contents of which are incorporated herein by reference.

FIELD

The present disclosure relates to compositions and methods of enhancing brain development and central nervous system (CNS) maturation of an individual. The compositions comprise a mixture of natural tocopherols, wherein the compositions contain an optimum tocopherol profile similar to that found in human breast milk, and can encompass a tocopherol profile from early stage to transitional to mature human breast milk. The present disclosure also relates to nutritional compositions having a tocopherol profile wherein a weight ratio range for RRR alpha-tocopherol to RRR gamma-tocopherol is from about 2:1 to about 20:1. The tocopherol mixture is typically added to a delivery vehicle such as powders, liquids, and nutritional formulas.

BACKGROUND

Maturation of the central nervous system ("CNS"), including the brain and eyes, is a key developmental area for the fetus and newborn. Accordingly, it is imperative that sufficient nutrition is provided in utero and after birth such that maturation may occur.

Infant formulas are commonly used today to provide a supplemental or sole source of nutrition early in life to both preterm and term infants. These formulas typically contain protein, carbohydrate, fat, vitamins, minerals, and other nutrients, and are commercially available as powders, ready-to-feed liquids, and liquid concentrates. Many infant formulas provide a quality alternative to human milk, as not all infants can receive human milk.

SUMMARY

This present disclosure relates generally to a method of enhancing brain development and CNS maturation in individuals, namely infants and preterm infants as defined herein, and protection from oxidative stress, by administering a mixture of optimized natural alpha- and gamma-tocopherols, optionally in combination with various vitamins, minerals and macronutrients, in a nutritional composition.

The nutritional composition may comprise fat, protein, carbohydrates, minerals and from about 5 mg/L to about 100 mg/L of an optimized tocopherol blend having a weight ratio of RRR alpha-tocopherol to RRR gamma-tocopherol of from about 2:1 to about 20:1, and less than about 8 mg/L of non-RRR alpha-tocopherol isomer. The weight ratio of RRR alpha-tocopherol to RRR gamma-tocopherol may also be from about 3:1 to about 15:1. The weight ratio of RRR alpha-tocopherol to RRR gamma-tocopherol may also be from about 4:1 to about 10:1. The weight ratio of RRR alpha-tocopherol to RRR gamma-tocopherol may also be about 5:1.

The nutritional composition may be an infant formula which may be a liquid or a powdered nutritional product. The composition may have from about 20 g/L to about 50 g/L fat, from about 10 g/L to about 15 g/L protein, and at least about 4 mg/L of RRR alpha-tocopherol. The composition may also comprise one or more materials including, but not limited to, a polyunsaturated fatty acid selected from arachidonic acid, docosahexaenoic acid, and a combination thereof, vitamin C, carotenoids, and trans-lutein.

The nutritional composition may be used to enhance brain development in individuals, namely infants and/or preterm infants, by administering a nutritional composition, in the form of an infant formula or a preterm infant formula, comprising: i) from about 20 g/L to about 50 g/L of fat; ii) from about 10 g/L to about 15 g/L of protein; wherein said fat includes oils comprising RRR alpha-tocopherol and RRR gamma-tocopherol, with a weight ratio of RRR alpha-tocopherol to RRR gamma-tocopherol ranging from about 3.5:1 to about 10:1; and iii) no more than about 8 mg/L of a non-RRR alpha-tocopherol isomer. The weight ratio of RRR alpha-tocopherol to RRR gamma-tocopherol may also be about 5:1. The nutritional composition may also comprise one or more materials selected from a carbohydrate, a polyunsaturated fatty acid, a carotenoid, vitamin C, trans-lutein, and a combination thereof.

The present disclosure also relates to a method of improving CNS maturation in individuals, namely infants and preterm infants. The present disclosure also relates to a method of improving CNS maturation and protection in individuals, namely infants and preterm infants, from oxidative stress by administering an optimized mixture of natural tocopherols comprising RRR alpha-tocopherol and RRR gamma-tocopherol, optionally in combination with various vitamins, minerals and macronutrients. For ease of administration and maximized efficacy, the optimized mixture of natural tocopherols are typically delivered in an oral dosage form with a limited level of non-RRR alpha-tocopherols to maximize the efficacy efficiency of the RRR alpha-tocopherol on stimulating postnatal CNS development.

DETAILED DESCRIPTION

The instant disclosure provides compositions and methods believed to have enhanced effects on cognitive, CNS, and/or brain development, due to an optimized mixture of natural tocopherols and limited levels of non-RRR alpha-tocopherol isomers. The gamma-tocopherol and non-RRR alpha-tocopherols may compete with RRR alpha-tocopherol for absorption and for lipoprotein at the intestine and liver level. In addition, these compounds may compete with RRR alpha-tocopherol for absorption into brain. Not wishing to be bound by the hypothesis, the applicants believe that RRR alpha-tocopherol binds TAP and the resultant complex up-regulate genes that regulate cholesterol, myelin protein and synaptic protein synthesis.

The term "retort packaging" and "retort sterilizing" are used interchangeably herein, and unless otherwise specified, refer to the common practice of filling a container, most typically a metal can or other similar package, with a nutritional liquid and then subjecting the liquid-filled package to the necessary heat sterilization step, to form a sterilized, retort packaged, nutritional liquid product.

The term "aseptic packaging" as used herein, unless otherwise specified, refers to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The term "infant" as used herein, refers generally to individuals up to age 36 months of age, actual or corrected.

The term "preterm infant" as used herein refers to those infants born at less than 37 weeks gestation, have a birth weight of less than 2500 gm, or both.

The term "as-fed basis" as used herein, unless otherwise specified, refers to feeding the infant a suitable nutritional formula in liquid form, which has been properly reconstituted from substances such as liquids, gels, powders and the like; these substances may be reconstituted with human milk or formula, in addition to water, diluted concentrates, and manufactured liquids. In one example, an "as-fed" basis may refer to feeding an infant or preterm infant the human milk fortifier after mixing the human milk fortifier with human milk in the ratio of 1 part human milk fortifier to 5 parts human milk.

The terms "ready-to-feed" and "RTF" refer to a formula that may be consumed without requiring additional compositional changes prior to consumption. For example, an RTF infant formula may be fed directly to the infant without having to mix with water or another fluid, as would be the case with powdered formulas or concentrated forms of liquid products.

As used herein, all concentrations expressed as either "mcg/liter" or "mg/liter" refer to ingredient concentrations within the described infant formulas as calculated on an as-fed basis or the concentrated human milk fortifier, unless otherwise specified.

The terms "fortifier solids" and "total solids," unless otherwise specified, are used interchangeably herein and refer to all material components of the compositions of the present disclosure, less water.

The term "hypoallergenic" as used herein means that the concentrated liquid human milk fortifier has a decreased tendency to provoke an allergic reaction in a preterm or term infant as compared to non-hypoallergenic fortifiers.

The term "stable" as used herein means that the concentrated liquid human milk fortifier is resistant to separation and precipitation for time period after manufacture of at least three months, and preferably at least six months.

The terms "fat," "lipid," and "oil" as used herein, unless otherwise specified, are used to refer to lipid materials derived or processed from plants. These terms may also include synthetic lipid materials so long as such synthetic materials are suitable for oral administration to humans.

The terms "natural tocopherol ratio," "alpha- to gamma-tocopherol ratio," "vitamin E," "natural vitamin E," and "mixture of natural tocopherols" as used herein refers to the RRR alpha-tocopherol, RRR alpha-tocopherol acetate, RRR alpha-tocopherol succinate and RRR gamma-tocopherol, RRR gamma-tocopherol acetate, RRR gamma-tocopherol succinate forms and derivatives thereof.

The terms "nutritional composition," "nutritional product," and "nutritional formula" as used herein, unless otherwise specified, are used interchangeably to refer to nutritional liquids and nutritional powders that comprise at least one of protein, fat, and carbohydrate and are suitable for oral administration to a human. The nutritional composition may further comprise vitamins, minerals, and other ingredients and represent a sole, primary, or supplemental source of nutrition. Nutritional compositions include infant formulas.

The term "nutritional liquid," as used herein, unless otherwise specified, refers to nutritional products in ready-to-drink liquid form, concentrated form, and nutritional liquids made by reconstituting the nutritional powders described herein prior to use.

The term "nutritional powder," as used herein, unless otherwise specified, refers to nutritional products in flowable or scoopable form that can be reconstituted with water or another aqueous liquid prior to consumption and includes both spray dried and dry mixed/dry blended powders.

All percentages, parts and ratios as used herein, are by weight of the total composition, unless otherwise specified. All such weights as they pertain to listed ingredients are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth. All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The various embodiments of the nutritional compositions of the present disclosure may also be substantially free of any ingredient or feature described herein, provided that the remaining formula still contains all of the required ingredients or features as described herein. In this context, and unless otherwise specified, the term "substantially free" means that the selected composition contains less than a functional amount of the optional ingredient, typically less than 1%, including less than 0.5%, including less than 0.1%, and also including zero percent, by weight of such optional or selected essential ingredient.

The nutritional compositions may comprise, consist of, or consist essentially of the elements of the products as described herein, as well as any additional or optional element described herein or otherwise useful in nutritional product applications.

All referenced patents and applications are incorporated herein by reference in their entirety. Where a definition or use of a term in an incorporated reference is inconsistent or contrary to the definition of that term provided herein, the definition of that term provided herein applies and the definition of that term in the reference does not apply.

The Food and Nutrition Board (FNB) previously issued an edition of "DRI: Dietary Reference Intakes for Vitamin C, Vitamin E, Selenium, and Carotenoids" (Washington, D.C.: National Academy of Sciences. 2000), in which the occurrence, adequate intake, and biological activity of vitamin E are summarized in detail. It is emphasized that there are two groups of compounds found in plant materials that have vitamin E biological activity, that is, tocopherols and tocotrienols. The tocopherols are characterized by a substituted, hydroxylated ring system (chromanol ring) with a long, saturated (phytyl) side chain. Tocotrienols differ from tocopherols only in that they have an unsaturated side chain. The naturally occurring tocopherols include alpha-, beta-, gamma-, and delta-tocopherols. These various forms are not interconvertible in the human and thus do not behave the same metabolically. The FNB limits the vitamin E activity of alpha-tocopherol to that available from the naturally occurring form (RRR-) and the other three synthetic 2R-stereoisomer forms (RSR-, RRS-, and RSS-) of alpha-tocopherol for purposes of establishing the human requirement for vitamin E. Other natural occurring forms of vitamin E (beta-, gamma-, delta-tocopherols and the tocotrienols) do not contribute toward meeting the vitamin E requirement because, although absorbed, there are not converted to alpha-tocopherol by humans and are recognized poorly by the alpha-tocopherol transfer protein in the liver.

Based on a review of the data by the FNB, the 2R-stereoisomeric forms of alpha-tocopherol (RSR-, RRS-, and RSS-) were used to estimate the vitamin E requirement. Thus, the Estimated Average Requirements (EARs), Recommended Dietary Allowances (RDAs), and Adequate Intakes (AIs) that are listed below apply only to intake of the 2R-stereoisomeric forms of alpha-tocopherol from food, fortified food and multivitamins. The Upper Limits (ULs) apply to any forms of supplemental alpha-tocopherol. The FNB found no functional criteria of vitamin E status that reflected the response to dietary intake in infants. Thus, the recommended intakes of vitamin E are based on AIs, which reflects a calculated mean vitamin E intake of infants fed principally with human milk. The UL was judged not determinable by the FNB because of insufficient data on adverse effects in this age group. Table 1 lists the Adequate Intake (AI) for infants ages 0 through 12 months.

TABLE 1

Infant Adequate Intake for Vitamin E

| Infants (ages) | AI (alpha-tocopherol) |
| --- | --- |
| 0-6 months | 4.0 mg/day (~0.6 mg/kg) |
| 7-12 months | 5.0 mg/day (~0.6 mg/kg) |

RRR Alpha-Tocopherol

It is imperative that early in life infants receive sufficient nutrition to provide for adequate maturation both physically and mentally, and specifically in the brain and central nervous system. Insufficient nutrition can result in numerous health problems that can be life-long in many individuals. In particular, brain and central nervous system maturation are key developmental areas for infants.

Our brain analysis showed a correlation between cholesterol, glutamate, and RRR alpha-tocopherol. Cholesterol is a major component of myelin, and thus, is a marker for extent of CNS myelination. Glutamate is a neurotransmitter, which is reported to stimulate neuron outgrowth and branching. Our discoveries suggest that RRR alpha-tocopherol stimulate new born infant CNS development. Accordingly, an excessively high level of dietary gamma-tocopherol may hinder the brain uptake of RRR alpha-tocopherol, and thus, may hinder CNS development.

Brain accretion of RRR alpha-tocopherol enhances CNS maturation and cognition. That is, the presence of RRR alpha-tocopherol in the brain of a human infant enhances the maturation of the infant's central nervous system and cognitive development. The brains of breast fed infants have a higher level of myelination as indicated by the higher lipid and cholesterol content. It has been observed that although formula and breast milk fed infants have about the same level of alpha-tocopherol, formula fed infants have more non-RRR alpha-tocopherol. It has been reported that supernatant protein factor binds alpha-tocopherol, forming a complex that stimulates cholesterol synthesis, and thus, myelination. It is the belief of the Applicant that non-RRR alpha-tocopherol isomers compete with RRR alpha-tocopherol for the binding sites on supernatant protein factor activity, resulting in a decrease in the beneficial effect of RRR alpha-tocopherol on CNS maturation by such competition. In other words, efficacy of RRR alpha-tocopherol in obtaining these effects is believed to be dependent, in part, on the ability of RRR alpha-tocopherol to form a complex that exerts the desired effect, and that non-RRR alpha-tocopherol isomers reduce RRR alpha-tocopherol efficacy by interfering with this binding.

Thus, the Applicants have surprisingly found that by limiting the amount of non-RRR alpha-tocopherol isomers, the efficacy of RRR alpha-tocopherol in enhancing cognitive, brain and/or CNS development is increased. It is believed that by enhancing the effect of RRR alpha-tocopherol isomers using the nutritional compositions described herein, the CNS maturation of an infant may be enhanced and improved through improved neuron myelination via cholesterol synthesis.

It is further believed that the presence of elevated levels of RRR alpha-tocopherol in the brain correlates with the production of glutamate in the brain. Glutamate is shown to stimulate neurite outgrowth and branching. Neurite outgrowth and branching allow neuron cells to establish new gap junctions. Increased neuronal communication via newly formed gap junctions may allow the brain to process more data in a given period of time. Accordingly, maximizing RRR alpha-tocopherol efficacy can improve overall brain health. Thus, it is believed that by these mechanisms at a minimum, the presence of RRR alpha-tocopherol plays an important role in the brain development of the fetus or newborn.

As used herein, the term "RRR alpha-tocopherol" refers to both exogenous sources and inherent sources of RRR alpha-tocopherol and RRR alpha-tocopherol acetate that are present in a nutritional composition, including an infant formula. Inherent sources include RRR alpha-tocopherol that is inherently present in components that are present in a nutritional composition and may include for example, various oils and fats. Exogenous sources of RRR alpha-tocopherol include RRR alpha-tocopherol that is added to the nutritional composition not as part of another component.

Tocopherols, generically referred to as vitamin E, are available in four forms: alpha-, beta-, gamma-, and delta-, which differ in the number and position of the methyl groups on the chroman ring, as shown by the structure below and Table 2.

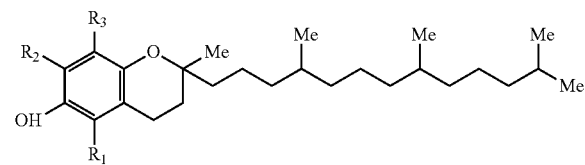

TABLE 2

Structure of Natural Tocopherols

| Compound | $R_1$ | $R_2$ | $R_3$ |
|---|---|---|---|
| alpha-tocopherol | Me | Me | Me |
| beta-tocopherol | Me | H | Me |
| gamma-tocopherol | H | Me | Me |
| delta-tocopherol | H | H | Me |

Further, tocopherols can exist in a number of stereoisomeric forms depending on the chirality of the phytyl tail. Of the alpha-tocopherols, RRR alpha-tocopherol (also referred to as "natural vitamin E") has the greatest biological activity and is reported to be the dominant form of the alpha-tocopherol in the brain. RRR alpha-tocopherol is a single stereoisomer whereas synthetic vitamin E (all-rac-alpha-tocopherol or tocopherol acetate) is an equimolar mixture of eight isomers, only one of which is RRR alpha-tocopherol. The fact that the dominant form of alpha-tocopherol is RRR alpha-tocopherol (based on animal studies) strongly suggests that the other seven chiral isomers must be absorbed at a lower rate by the brain or oxidized at a faster rate.

Both free tocopherol and its acetate ester are water-insoluble, nonswelling amphiphiles, as are triglycerides and cholesterol. Thus, many of the factors and processes necessary for the absorption of dietary lipids are also required for absorption of tocopherols. These factors include: efficient emulsification, solubilization within mixed bile salt micelles, uptake by the small intestinal cell (enterocyte), packaging within lipoprotein particles (chylomicrons) and secretion into the circulation via the lymphatic system.

Tocopherols must be emulsified and solubilized before their absorption across the brush-border membrane of the enterocyte. Emulsification begins in the stomach by predominantly mechanical forces that break up large emulsion particles into smaller particles. Within the small intestine chyme mixes with pancreatic and biliary secretions, pancreatic lipase hydrolyzes triglyceride into monoglycerides and fatty acids. These lipolytic products ferry the lipid soluble vitamins in the oil phase into the aqueous digesta. Together with bile salts and free fatty acids and monoglycerides from triglyceride (TG) digestion, they form molecular aggregates known as mixed micelles. These mixed micelles diffuse across the unstirred water layer to reach the brush-border membrane of the enterocyte and the lipotic products and the lipid soluble vitamins are absorbed.

The uptake of fatty acids and lipid soluble nutrients such as carotenoids and tocopherol by the enterocyte are thought to be via passive diffusion. However, recent research has indicated that the absorption of fatty acids and lipid soluble nutrients are via a facilitated process. In another word, these compounds are bound to a lipid transfer protein, then, transport across the microvilli membrane (Reboul et al., *J. Bio. Chem.* (2006), Vol. 281:4739). Reboul et al. (2006) suggest that tocopherol absorption is, in part, facilitated by Scavenger Receptor Class B Type 1 (SRB1). Thus, there will be competition for intestinal absorption between gamma- and alpha-tocopherol. Within the enterocyte, the tocopherols are incorporated into chylomicrons and secreted into the intracellular spaces and lymphatics and thus into the bloodstream.

Supplements of vitamin E are generally given in the form of alpha-tocopherol acetate in which the relative hydroxyl group of alpha-tocopherol is esterified, rendering the molecule more stable than the free form. Tocopherol acetate is digested by pancreatic esterase. The resultant free tocopherols are then ferried into the aqueous phase of digesta by the free fatty acids from triglycerides digestion. It is known that both alpha- and gamma-tocopherols are absorbed by the enterocyte and packaged into chylomicron.

Portions of the tocopherols in the chylomicron are transported to the adipose tissue by the free fatty acids from chylomicron triglyceride (TG) digestion. Chylomicrons are quickly digested by serum lipoprotein lipase. The tocopherols in the remnant chylomicron is absorbed into liver and digested. The released tocopherols are bound by tocopherol transfer protein and deliver to Golgi body to be packaged into very low density lipoprotein (VLDL), low density lipoprotein (LDL), and high density lipoprotein (HDL) to re-enter circulation. The half life of LDL and HDL are much longer than chylomicron and LDL, thus, most of the tocopherols and carotenoids in circulations are associated with lipoproteins. A high level of gamma tocopherol in the liver may compete with alpha-tocopherol for LDL and HDL. Thus, a high level of gamma tocopherol may reduce the bio-availability of alpha-tocopherol.

It is well established that alpha and gamma tocopherols function as an in vivo antioxidant, protecting lipids against peroxidative damage and it is known that red blood cells (RBCs) from newborns are more sensitive to in vitro oxidative stress than adult RBCs. Most of the intracellular hemoglobin (HB) in neonatal RBCs is fetal hemoglobin (HBF), which has a stronger tendency to denature and oxidize than adult hemoglobin (HBA). Denatured and oxidized HB is a potent catalyst for lipid peroxidation. Further, exposure to free radicals places the preterm infant at risk for diseases of prematurity including intraventricular hemorrhage, retinopathy of prematurity, bronchopulmonary dysplasia and necrotizing enterocolitis.

It has been reported that the RRR alpha-tocopherol content and alpha- to gamma-tocopherol ratio of human milk decrease with stage of lactation. The alpha- to gamma-tocopherol ratio of colostrum is about 10 and it decreases to about 4-6 in mature milk. It is possible that these alpha- to gamma-tocopherol ratios are optimized for maximum protection of infant from oxidative stress without adversely affecting infant CNS development.

The RRR alpha-tocopherol may be present in the nutritional compositions in an amount sufficient to improve brain or CNS development. In some aspects, the nutritional compositions may comprise RRR alpha-tocopherol in concentrations of at least about 5 mg/L, including at least about 7 mg/L, including at least about 8 mg/L, including at least about 9 mg/L, including at least about 10 mg/L, including at least about 15 mg/L, including at least about 18 mg/L, including at least about 20 mg/L, including from at least about 5 mg/L to about 100 mg/L, including from at least about 7 mg/L to about 50 mg/L, and including from about 20 mg/L to about 40 mg/L. The total amounts of RRR alpha-tocopherol include both exogenous and inherent sources of RRR alpha-tocopherol, as noted above.

Our brain analysis work showed over 60% of the alpha-tocopherol in formula fed infant brain is RRR alpha-tocopherol. Most commercial infant formulas are fortified with synthetic alpha-tocopherols. It has been reported that the plasma contraction of the 2R isomers are about equal for animals fed a diet containing synthetic alpha-tocopherols. These findings indicate that RRR alpha-tocopherol is preferably absorbed into the brain or it is metabolized at a much slower rate than RSR, RRS and RSS tocopherols.

It is reported that tocopherol association protein (TAP) binds tocopherol and the resultant complex translocates into cell nucleus to regulate gene expression. These findings lead the applicant to believe that TAP preferably binds RRR alpha-tocopherol and this complex formation prevent the RRR alpha-tocopherol from being metabolized or oxidized. Thus, RRR alpha-tocopherol is metabolized at a slower rate than other 2R isomers. In other words, applicants believe that RRR alpha-tocopherol is more potent than the other 2R isomers in stimulating CNS maturation. Accordingly, applicants believe that the presence of a high level of non-RRR alpha-tocopherol isomers will compete with RRR alpha-tocopherol for the tocopherol association protein, thus compromising the efficacy of RRR alpha-tocopherol. Based upon these findings, the applicants believe that an optimized blend of tocopherols should provide an infant: 1) no less than 0.25 mg/Kg body weight/day of RRR alpha-tocopherol; 2) appropriate levels of RRR gamma-tocopherol so that the alpha- to gamma-tocopherol ratio ranges from 2:1 to 20:1; and 3) less than 0.4 mg of non-RRR alpha-tocopherol isomers.

It has been discovered that non-RRR alpha-tocopherol isomers may compete with RRR alpha-tocopherol for absorption into brain. In other words, non-RRR alpha-tocopherol acts as an agonist of RRR alpha-tocopherol, because the presence of high levels of non-RRR alpha-tocopherol can compromise its beneficial effects. Thus, by limiting the non-RRR alpha-tocopherol chiral isomers and combining RRR alpha-tocopherol with other enhancers of CNS development in specific combinations and amounts, a synergistic impact on the development of the brain and CNS of the fetus, and breast-feeding newborn may occur.

In some embodiments, the nutritional compositions include another additional tocopherol, particularly RRR gamma-tocopherol, in addition to the RRR alpha-tocopherol. RRR gamma-tocopherol has been used in food applications as an antioxidant, thereby preventing deterioration of foods and beverages resulting from oxidation of susceptible components such as some fats.

RRR gamma-tocopherol, however, has now been found to negatively correlate with phospholipids. Accordingly, when present, the RRR gamma-tocopherol may be present in the infant formulas in concentrations of less than 7 mg/L, including less than 5 mg/L, including from 0 mg/L to 3 mg/L including from about 1 mg/L to 3 mg/L of the nutritional composition.

The nutritional compositions of the present disclosure may include vitamin C in addition to the RRR alpha-tocopherol to provide oxidative protection. Vitamin C, also referred to as L-ascorbic acid or L-ascorbate, is available from many fruit and vegetable sources. Any source of vitamin C that is suitable for use in an oral nutritional product and is compatible with the essential elements and features of such products may be used with the nutritional compositions of the present disclosure.

Vitamin C may chelate free ferrous iron, which has been found to lower serum vitamin E levels in formula fed preterm infants, thereby preventing iron from acting as a pro-oxidant. Further, high levels of arachidonic acid (ARA) and docosahexaenoic acid (DHA) may generate high levels of lipid peroxides due to oxidation induced by intestine xanthin oxidase (XO), which can also degrade RRR alpha-tocopherol before RRR alpha-tocopherol can be absorbed in the gut. Accordingly, vitamin C may be included in the infant formulas of the present disclosure to reduce the oxidative degradation of RRR alpha-tocopherol. In this aspect, the nutritional compositions of the present disclosure may include vitamin C in a concentration of at least 130 mg/L, including at least 150 mg/L, including at least 175 mg/L, including at least 200 mg/L, including at least 225 mg/L, including at least 250 mg/L, including at least 300 mg/L and including from 130 mg/L to about 1000 mg/L, and including from about 200 mg/L to about 500 mg/L.

Non-RRR Alpha-Tocopherol Isomer

As used herein, the term "non-RRR alpha-tocopherol isomer" is intended to mean any stereoisomer of alpha-tocopherol that is not in the RRR configuration as will be readily understood by one of ordinary skill in the art.

The nutritional compositions disclosed herein may, in some aspects, be substantially free of non-RRR alpha-tocopherol isomers. In other aspects, the composition may comprise less than about 9 mg/L, or less than about 8 mg/L, or less than about 7 mg/L, or less than about 6 mg/L, or less than about 5 mg/L, or less than about 4 mg/L, or less than about 3 mg/L, or less than about 2 mg/L, or less than about 1 mg/L, or less than about 0.5 mg/L of non-RRR alpha-tocopherol isomers. In other aspects, the amount of non-RRR alpha-tocopherol isomers are limited to an amount that allows RRR alpha-tocopherol to effectively enhance brain, CNS, and/or cognitive development in an individual, particularly an infant. In one aspect, the compositions may be substantially free of non-RRR alpha-tocopherol isomers.

Vitamin E Activity

The eight known tocopherols have different biological activities. The naturally occurring RRR alpha-tocopherol has been assigned an activity of 1 mg alpha-tocopherol equivalent (TE) per milligram. The relative activities of other tocopherols are listed in Table 3. The vitamin E activity of a food may be calculated by taking the sum of the values obtained by multiplying the number of milligrams of each component tocopherol by the appropriate factor given in Table 3.

TABLE 3

Vitamin E Activity of the Tocopherols and Tocotrienols**

| Tocopherol | Activity as alpha-TE* (mg/mg compound) |
|---|---|
| RRR alpha-tocopherol | 1.0 |
| RRR beta-tocopherol | 0.5 |
| RRR gamma-tocopherol | 0.1 |
| RRR delta-tocopherol | 0.03 |
| RRR alpha-tocotrienol | 0.3 |
| RRR beta-tocotrienol | 0.05 |
| RRR gamma-tocotrienol | — |
| RRR delta-tocotrienol | — |
| Synthetic alpha-tocopherol acetate | 0.74 |

*alpha-tocopherol equivalents (TE)
**Table from Vitamin E in Health and Disease, edited by Lester Packer and Jurgen Fuchs; Marcel Dekker, Inc, New York, New York, 1993, p. 21
Dashes denote unknown activities Alpha- to Gamma-Tocopherol Ratio The instant invention relates to a method of improving CNS maturation in an infant by administering the required amount of vitamin E to said infant in an alpha- to gamma-tocopherol ratio from about 2:1 to about 20:1, or from about 3.5:1 to about 15:1; or from about 5:1 to about 10:1. Vitamin E or a source thereof having an alpha- to gamma-tocopherol ratio from about 2:1 to about 20:1 is also referred to herein as "an optimized tocopherol blend."

Alternatively, isolated alpha- and/or gamma-tocopherol components may be admixed with oil rich in alpha- and/or gamma-tocopherol. Based on the known tocopherol content of different oils, one skilled in the art would be able to select a fat source or blend of fats which when supplemented with alpha- and/or gamma-tocopherol will achieve the desired alpha- to gamma-tocopherol ratio of the instant invention.

For example, alpha-tocopherol is blended with a fat system rich in gamma-tocopherol. Commercial sources for isolated alpha- and gamma-tocopherol are readily available and known to one practicing the art. For example, RRR alpha-tocopherol and RRR alpha-tocopherol acetate are available from Eastman Chemical Corp. of Kingsport, Tenn.

The tocopherol ratio described above may be delivered in any acceptable oral dosage form. One knowledgeable in the art would be able to select an appropriate carrier to aid in the ease of administration and to improve the organoleptic properties depending on the target population, e.g., infants. The alpha- to gamma-tocopherol ratio of the present invention may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24-hour period. An infant may receive an alpha- to gamma-tocopherol ratio from about 2:1 to about 20:1, or from about 3.5:1 to about 15:1; or from about 5:1 to about 10:1, for example, as a concentrated liquid or infant nutritional supplement.

In one embodiment, a nutritional composition of the present disclosure comprises fat, protein, carbohydrates, minerals, and from about 5 mg/L to about 100 mg/L of an optimized tocopherol blend having a weight ratio of RRR alpha-tocopherol to RRR gamma-tocopherol of from about 2:1 to about 20:1, and less than about 8 mg/L of non-RRR alpha-tocopherol isomer. In certain embodiments, the nutritional composition comprises from about 7 mg/L to about 75 mg/L of the optimized tocopherol blend, including from about 10 mg/L to about 50 mg/L, and also including from about 20 mg/L to about 40 mg/L of the optimized tocopherol blend.

The nutritional compositions of the present disclosure generally contain less than about 8 mg/L of non-RRR alpha-tocopherol isomer. In certain embodiments, the nutritional compositions of the present disclosure comprise less than about 5 mg/L of non-RRR alpha-tocopherol isomer, including less than about 1 mg/L of non-RRR alpha-tocopherol isomer, and also including less than about 0.5 mg/L of non-RRR alpha-tocopherol isomer. In other embodiments, the nutritional compositions of the present disclosure are substantially free of non-RRR alpha-tocopherol isomer.

The optimized tocopherol blend of the present disclosure comprises a weight ratio of RRR alpha-tocopherol to RRR gamma-tocopherol of from about 2:1 to about 20:1. In certain embodiments, the nutritional composition comprises an optimized tocopherol blend having a weight ratio of RRR alpha-tocopherol to RRR gamma-tocopherol ranging from about 3:1 to about 15:1. In certain embodiments, the nutritional composition comprises an optimized tocopherol blend having a weight ratio of RRR alpha-tocopherol to RRR gamma-tocopherol ranging from about 4:1 to about 10:1. In certain embodiments, the nutritional composition comprises an optimized tocopherol blend having a weight ratio of RRR alpha-tocopherol to RRR gamma-tocopherol of about 5:1.

In certain embodiments, the nutritional compositions of the present disclosure include (i) from about 20 g/L to about 50 g/L f; (ii) from about 10 g/L to about 15 g/L protein; and at least about 4 mg/L of RRR alpha-tocopherol.

The nutritional compositions of the present disclosure may also comprise one or more materials including, but not limited to, a polyunsaturated fatty acid selected from arachidonic acid, docosahexaenoic acid, and a combination thereof, vitamin C, and a carotenoid, such as trans-lutein.

The nutritional compositions of the present disclosure may be formulated in a wide variety of product forms. In one embodiment, the nutritional composition is a liquid nutritional product. In another embodiment, the nutritional composition is a powdered nutritional product. In one embodiment, the nutritional composition is an infant formula. In another embodiment, the nutritional composition is a preterm infant formula.

Infant Dietary Supplement

The alpha- to gamma-tocopherol ratio of the instant invention may be delivered to an infant in the form of a concentrated liquid, reconstitutable particles, and microparticles, for example. Syrups, honeys and elixirs may be admixed with the natural tocopherol ratio to improve the flavor. Oil in water emulsions may be better suitable for oral use in infants because these are water-miscible and thus their oiliness is masked. Emulsions are well known in the pharmaceutical sciences. The supplement of this invention can be manufactured using techniques well known to those skilled in the art. Generally speaking, an emulsifying agent is dissolved in the oil. The emulsifier/oil mixture may be added directly to the water to form an oil-in-water emulsion. Alternatively, the emulsifying agent is dissolved in the water and the oil is added, with agitation, to the emulsifier/aqueous solution. Examples, of typical natural emulsifying agents include gelatin, egg yolk, casein, wool fat, cholesterol, acacia, tragacanth, chondrus and pectin. The mixtures require physical manipulation to achieve the emulsified physical state. Emulsification equipment includes a wide variety of agitators, homogenizers, colloid mills and ultrasonic devices.

The alpha- and gamma-tocopherol emulsion of the instant invention may be stored in conventional containers and are dispensed in small but precise quantities or unit dosages. Such dosages are characteristically dispensed using a pipette and compressible, resilient bulb dropper assembly.

As discussed above, the FNB recommends a dose of 0.6 mg/kg of infant body weight per day for vitamin E. Typically the amount of liquid required to provide a unit dose of the alpha- and gamma-tocopherol emulsion will typically range from about 0.1 ml to about 8 ml, more preferably from about 0.5 ml to about 5.0 ml, most preferably from about 0.5 ml to about 2.0 ml.

The infant dietary supplement of the present inventive subject matter may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period.

Typically, a unit dose of the infant dietary supplement of the invention comprises at least 50% of the AI for vitamin E for infants in the alpha- to gamma-tocopherol ratio of the invention in about 1 ml. Typically, a unit dose is administered to the infant at least once a day.

Additional nutrients may be added to the alpha- and gamma-tocopherol dietary supplement. Optional nutrients may include a blend of antioxidants such as trans beta-carotene, cis beta-carotenes, cis alpha-carotenes, trans lycopene, cis lycopene, trans gamma-carotene, cis gamma-carotene, zeta-carotene, phytofluene, phytoene, vitamin C, cis lutein, trans lutein, cis lutein esters, trans lutein esters, cis zeaxanthin, trans zeaxanthin, cis zeaxanthin ester, trans zeaxanthin ester, beta crytoxantyhin and glutamine and other nutrients such as vitamin A, vitamin $B_1$, vitamin $B_2$, vitamin $B_6$, vitamin $B_{12}$, vitamin C, vitamin D, vitamin K, biotin, folic acid, pantothenic acid, niacin, m-inositol, calcium, phosphorus, magnesium, zinc, manganese, copper, sodium, potassium, chloride, iron, chromium, molybdenum, and selenium.

An optional infant dietary supplement of the instant invention typically supplies about 80% of the AI for vitamin E for infants in the alpha- to gamma-tocopherol ratio of the invention per day, from about 65 to 145 mcg/day beta-cryptoxanthin, from about 100 to about 145 mcg/day lycopene, from about 40 to about 80 mcg/day alpha-carotene, from about 175 to about 355 mcg/day beta-carotene and from about 175 to about 355 mcg/day lutein/zeaxanthin. Typically, 1 ml is a unit dose which is administered to the infant at least once a day. Alternatively, the optimized tocopherol blend of the instant invention may be added to a nutritional composition, such as an infant nutritional formula.

Infant Nutritional Formula

Infant formulas are known in the art and one knowledgeable in the art would be able to adjust the formula to include the alpha- to gamma-tocopherol ratio of the instant invention. For example, an infant formula typically contains a protein component comprising from about 6 to about 25% of the total caloric content of said infant formula; a carbohydrate component comprising from about 35 to about 50% of the total caloric content of said infant formula; and a lipid component comprising from about 30 to about 50% of the total caloric content of said infant formula. These ranges are provided as examples only, and are not intended to be limiting. The fat component of an infant formula is an ideal source of energy for infants, not only because of its high caloric density but also because of its low osmotic activity in solution. The fat component also solubilizes fat-soluble vitamins and emulsifiers in the aqueous solution.

Based on the known tocopherol content of different oils, one skilled in the art would be able to select a fat source or blend of fats to achieve the desired alpha- to gamma-tocopherol ratio of the instant invention as well as meet the desired fatty acid profile for the specific application. Suitable fats will be readily apparent to those skilled in the art.

Alternatively, isolated alpha- and gamma-tocopherol may be individually added to a fat system to achieve the desired alpha- to gamma-tocopherol ratio.

One knowledgeable in the art would understand that appropriate additional amounts of vitamin E may need to be provided to nutritional compositions to compensate for some loss during processing and storage of such compositions. Practitioners would also understand that the degree of unsaturation of the component oils must be considered when calculating the required amount of vitamin E. A predictable amount of the Vitamin E would be required to prevent oxidation of the component oils in the nutritional product.

Additional components of the infant formula typically include, for example, protein, carbohydrates, vitamins and minerals. Protein is needed for growth, synthesis of enzymes and hormones, and replacement of protein lost from the skin and in urine and feces. These metabolic processes determine the need for both the total amount of protein in a feeding and the relative amounts of specific amino acids. The adequacy of the amount and type of protein in a feeding for infants is determined by measuring growth, nitrogen absorption and retention, plasma amino acids, certain blood analytes and metabolic responses.

The proteins that may be utilized in the infant nutritional products of the invention include any proteins or nitrogen source suitable for human consumption. Such proteins are well known by those skilled in the art and can be readily selected when preparing such products. Examples of suitable protein sources for an infant typically include casein, whey, condensed skim milk, nonfat milk, soy, pea, rice, corn, hydrolyzed protein, free amino acids, protein sources which contain calcium in a colloidal suspension with the protein. Any single protein listed above, or any combination thereof, as appropriate may be utilized. Other suitable proteins will be readily apparent to those skilled in the art.

A preferred protein system typically comprises 7% whey protein concentrate and 93% nonfat milk.

Commercial protein sources are readily available and known to one practicing the art. For example, caseinates, whey, hydrolyzed caseinates, hydrolyzed whey, and milk proteins are available from New Zealand Milk Products of Santa Rosa, Calif. Soy and hydrolyzed soy proteins are available from Protein Technologies International of Saint Louis, Mo. Pea protein is available from Feinkost Ingredients Company of Lodi, Ohio. Rice protein is available from California Natural Products of Lathrop, Calif. Corn protein is available from EnerGenetics Inc. of Keokuk, Iowa. Additionally, mineral enriched proteins are available from New Zealand Milk Products of Santa Rosa, Calif. and Protein Technologies International of Saint Louis, Mo.

An additional component of the infant formula of this invention is a source of carbohydrates. Carbohydrates are a major source of readily available energy that the infant needs for growth and that protects the infant from tissue catabolism. In human milk and most standard milk-based infant formulas, the carbohydrate is lactose.

The carbohydrates that may be used in the infant formula can vary widely. Examples of carbohydrates suitable for infants typically include hydrolyzed cornstarch, maltodextrin, glucose polymers, sucrose, lactose, corn syrup, corn syrup solids, rice syrup, glucose, fructose, high fructose corn syrup and indigestible oligosaccharides such as fructooligosaccharides (FOS). Any single carbohydrate listed above, or any combination thereof, as appropriate may be utilized. Other suitable carbohydrates will be readily apparent to those skilled in the art.

Typically, lactose is the preferred carbohydrate source that comprises 100% of the carbohydrate component.

Commercial sources for the carbohydrates listed above are readily available and known to one practicing the art. For example, corn syrup solids are available from Cerestar USA, Inc. in Hammond, Ind. Glucose and rice based syrups are available from California Natural Products in Lathrop, Calif. Various corn syrups and high fructose corn syrups are available from Cargill in Minneapolis, Minn. Fructose is available from A. E. Staley in Decatur, Ill. Maltodextrin, glucose polymers, and hydrolyzed corn starch are available from American Maize Products in Hammond, Ind. Sucrose is available from Domino Sugar Corp. in New York, N.Y. Lactose is available from Foremost in Baraboo, Wis., and indigestible oligosaccharides, such as FOS, are available from Golden Technologies Company of Golden, Colo.

The infant formula of the present invention typically includes supplemented vitamins and minerals.

Infants require the electrolytes sodium, potassium and chloride for growth and for acid-base balance. Sufficient intakes of these electrolytes are also needed for replacement of losses in the urine and stool and from the skin. Calcium, phosphorus and magnesium are needed for proper bone mineralization. For bones to grow, adequate amounts of these minerals must be present in a feeding. Infants may develop rickets or osteopenia if they do not receive adequate amount of calcium and phosphorus in their diet. Phosphorus and magnesium are also found in intracellular fluid. These minerals are needed for the growth and function of soft tissue.

Trace minerals are associated with cell division, immune function and growth. Consequently, provision of sufficient amounts of trace minerals is needed for rapid growth in infants. Another trace mineral, iron, is important for the synthesis of hemoglobin, myoglobin, and iron-containing enzymes. However, it is not certain that infants need the recommended amounts of iron during the first 2 months of life. Also, it is estimated that infants have sufficient iron stores without receiving iron supplementation, if blood loss is small, until 2 months of age. Consequently, the infant formula of the instant invention may be optionally fortified with iron. Zinc is needed for growth, for the activity of numerous enzymes, and for DNA, RNA and protein synthesis. Copper is necessary for the activity of several important enzymes. Manganese is needed for the development of bone and cartilage and is important in the synthesis of polysaccharides and glycoproteins.

Vitamin A is a fat-soluble vitamin essential for normal bone formation and for maintenance of specialized epithelial surfaces, which include mucous membranes of the eyes; the mucosa of the respiratory, gastrointestinal and genitourinary tracts; the ducts of various glands; and the skin, hair, gums and teeth. Vitamin D is important for absorption of calcium and to a lesser extent, phosphorus, and for the development of bone. Vitamin K is important in the biosynthesis of prothrombin and other blood-clotting factors. Newborn infants have little reserve of vitamin K and do not have a source for vitamin K until after intestinal bacteria are established, thereby becoming an important source of vitamin K for the infant. Vitamin E (tocopherol) prevents peroxidation of polyunsaturated fatty acids in the cell, thus preventing tissue damage. Infants may develop hemolytic anemia and vitamin E deficiency when fed feedings low in vitamin E and high in iron and polyunsaturated fatty acids.

Vitamin C is necessary in the formulation of collagen and dentine and is required for the metabolic reactions of amino acids and for the synthesis of anti-inflammatory steroids by the adrenal glands. Folic acid is important in amino acid and nucleotide metabolism. Serum folate concentrations have been shown to fall below normal after 2 weeks of age in infants with low folic acid intakes. Thiamine (vitamin B1) functions as a coenzyme in oxidative metabolism. Riboflavin (vitamin B2) assists in the transfer of oxygen from plasma to substrate of tissue cells and also functions in hydrogen transport mechanisms. Niacin plays an essential role in the electron transport involved in cellular respiration and appears to be involved in pigment and fat metabolism. Pyridoxine (vitamin B6) functions as a coenzyme in amino acid decarboxylation, in transamination, and in tryptophan metabolism. Vitamin B12 is essential in the formulation of DNA, nuclear maturation, and cell division. Pantothenic acid functions as an important cofactor for all acylation reaction in the body. It is involved in gluconeogenesis, synthesis of fatty acids, and sterols, and cellular metabolism of fats, carbohydrates, and proteins.

Based on the requirements described above, the infant formula requires fortification to insure that a developing infant receives adequate amounts of vitamins and minerals while not over fortifying and possibly causing, for example, hypercalcemia. Using the recommendations of the FNB, one skilled in the art can readily calculate how much of a vitamin or mineral source should be added to the nutritional product in order to deliver the desired amount of a vitamin or mineral. Practitioners also understand that appropriate additional amounts of vitamin and mineral ingredients need to be provided to nutritional compositions to compensate for some loss during processing and storage of such compositions.

Examples of vitamins and minerals that may be added to the infant formula of the instant invention typically include vitamin A, vitamin $B_1$, vitamin $B_2$, vitamin $B_6$, vitamin $B_{12}$, vitamin C, vitamin D, vitamin K, vitamin E, biotin, folic acid, pantothenic acid, niacin, m-inositol, calcium, phosphorus, magnesium, zinc, manganese, copper, sodium, potassium, chloride, iron and selenium. The additional nutrients chromium, molybdenum, iodine, taurine, carnitine and choline may also require supplementation. As discussed above, the infant formula will include the natural form of vitamin E in the alpha- to gamma-tocopherol ratio of the instant invention.

Typically, 100% of the AI for vitamin E in the alpha- to gamma-tocopherol ratio of the instant invention is added to a liter of infant formula, which is a typical volume of formula consumed by an infant in a day.

The infant formula of this invention can be manufactured using techniques well known to those skilled in the art. While manufacturing variations are certainly well known to those skilled in the nutritional formulation arts, a few of the manufacturing techniques are described in detail in the Examples. Generally speaking a protein-in-oil blend is prepared containing all oils, any emulsifier, the fat-soluble vitamins and a portion of the protein. A second slurry is prepared by mixing the carbohydrate and minerals together. The protein-in-oil and any remaining protein are added to the carbohydrate/mineral slurry. The resulting mixture is homogenized, heat processed, standardized with water-soluble vitamins. The concentrated formula may be filled into appropriate packaging and sterilized; aseptically filled into sterile packaging; or dried and filled into appropriate packaging. The resulting powder may be milled to a specific particle size and/or agglomerated to modify particle size and mixability characteristics. Those skilled in the nutritional formulation arts would also be able to dry blend the individual starting materials and add the liquid ingredients through agglomeration or during the dry blending step. The concentrated blend may also be diluted and filled into appropriate packaging and sterilized or aseptically filled into sterile packaging.

Numerous types of packaging are readily available and known to one practicing the art. Desirable packaging characteristics include: effective protection against impact, light, and heat; ease of opening; and efficient sealing for storage stability.

Human Milk Fortifier

Premature infants require additional nutrients to support their growth and are at risk for the diseases related to prematurity related to oxidation. Therefore, a human milk fortifier would be a preferred vehicle to deliver the alpha- to gamma-tocopherol ratio of the instant invention. A human milk fortifier of this invention is a powder which when added to human milk delivers the preferred alpha- to gamma-tocopherol ratio and supplements the levels of protein, fat, vitamins and minerals.

Although not intended to limit the invention in any manner, but to merely serve as a general guideline, the human milk fortifier powder of this invention will typically provide the following macronutrient distribution. The protein component will typically be present in an amount of from about 24 wt/wt % to about 55 wt/wt % of the fortifier powder. The fat component will typically be present in an amount of from about 1 wt/wt % to about 30 wt/wt % of the fortifier powder. The carbohydrate component will typically be present in an amount of from about 15 wt/wt % to about 75 wt/wt % of the fortifier powder. Additionally, the amount of powder required to provide a unit dose of the fortifier will typically range from about 0.5 grams to about 10 grams of powder in a unit dose. The caloric density is typically from about 1.0 kcal/gram of powder to about 8.5 kcal/gram of powder.

The first component of the fortifier powder of this invention is a source of protein. As in the term infant, the preterm infant requires protein for growth, synthesis of enzymes and hormones, and replacement of protein lost from the skin and in urine and feces. These metabolic processes determine the need for both the total amount of protein in a feeding and the relative amounts of specific amino acids. The adequacy of the amount and type of protein in a feeding for infants is determined by measuring growth, nitrogen absorption and retention, plasma amino acids, certain blood analytes and metabolic responses.

As stated above, the protein component will typically be present in an amount of from about 24 wt/wt % to about 55 wt/wt % of the fortifier powder. The proteins that may be utilized in the nutritional products of the invention include any proteins or nitrogen source suitable for human consumption. Such proteins are well known by those skilled in the art and can be readily selected when preparing such products. Examples of suitable protein sources for a premature infant typically include casein, whey, condensed skim milk, nonfat milk, soy, pea, rice, corn, hydrolyzed protein, free amino acids, protein sources which contain calcium in a colloidal suspension with the protein. Any single protein listed above, or any combination thereof, as appropriate may be utilized. Other suitable proteins will be readily apparent to those skilled in the art.

The preferred protein system will typically be comprised of about 51 wt/wt % of the protein component as whey protein concentrate and about 49 wt/wt % of the protein component as nonfat dry milk, which corresponds to about 60 wt/wt % of the protein component as whey and about 40 wt/wt % of the protein component as casein.

Commercial protein sources are readily available and known to one practicing the art. For example, caseinates, whey, hydrolyzed caseinates, hydrolyzed whey and milk proteins are available from New Zealand Milk Products of Santa Rosa, Calif. Soy and hydrolyzed soy proteins are available from Protein Technologies International of Saint Louis, Mo. Pea protein is available from Feinkost Ingredients Company of Lodi, Ohio. Rice protein is available from California Natural Products of Lathrop, Calif. Corn protein is available from EnerGenetics Inc. of Keokuk, Iowa. Additionally, mineral enriched proteins are available from New Zealand Milk Products of Santa Rosa, Calif. and Protein Technologies International of Saint Louis, Mo.

The second component of the fortifier powder of this invention is a source of fat. Fat is an ideal source of energy for low birth weight (LBW) infants, not only because of its high caloric density but also because of its low osmotic activity in solution.

As stated above, the fat component will typically be present in an amount of from about 1 wt/wt % to about 30 wt/wt % of the fortifier powder. Suitable fats will be readily apparent to those skilled in the art Docosahexaenoic acid (DHA) is an omega-3 fatty acid and is thought to be essential for the proper brain and vision development of infants because it is the most abundant long chain polyunsaturated fatty acid (PUFA) in the brain and retina. Although a metabolic pathway exists in mammals for the biosynthesis of DHA from dietary linoleic acid, this pathway is bioenergetically unfavorable and mammals are thought to obtain most of their DHA from dietary sources. In the case of infants, the most likely source would be human milk. Indeed, DHA is the most abundant 20 carbon omega-3 PUFA in human milk. However, human milk DHA content will vary greatly depending on the diet of the mother. If the mother eats fish high in DHA often, her milk will contain higher DHA levels, while a mom with less access to fish will have lower DHA levels in her milk. Consequently, human milk may require DHA supplementation to insure that the preterm infant is receiving sufficient amounts of DHA. Preferably, DHA supplementation is accompanied by arachidonic acid (ARA) supplementation. U.S. Pat. No. 5,492,938 to Kyle et al. describes a method of obtaining DHA from dinoflagellates and its use in pharmaceutical composition and dietary supplements.

Typically, medium chain triglycerides (MCT) oil is the preferred fat source, which comprises 100% of the fat component. This fat source, at this level provides well-tolerated fat calories to the premature infant in addition to providing a vehicle for the desired alpha- to gamma-tocopherol ratio of the invention, other fat-soluble vitamins and emulsifiers. Since MCT oil (e.g., fractionated coconut oil) contains negligible levels of alpha- and gamma-tocopherol, the human milk fortifier is fortified with isolated alpha- and gamma-tocopherol to achieve the alpha- to gamma-tocopherol ratio of the instant invention.

An emulsifier is typically incorporated into the fortifier powder. Emulsifiers help the water soluble and insoluble components of the fortifier powder incorporate into the human milk. Examples of suitable emulsifiers typically include soya bean lecithin, polyoxythylene stearate, polyoxyethylene sorbitan mono-oleate, polyoxyethylene sorbitan monopalmitate, polyoxyethylene sorbitan monostearate, ammonium phosphatides, polyoxyethylene sorbitan monolaurate, citric acid esters of mono and diglycerides of fatty acids, tartaric acid esters of mono and diglycerides of fatty acids.

The preferred emulsifier source is natural soy lecithin. The amount of emulsifier will typically be present in an amount of from about 1 wt/wt % to about 10 wt/wt % of the fat component, which corresponds to about 0.1 wt/wt % to about 1 wt/wt % of the fortifier powder.

Numerous commercial sources for the emulsifiers listed above are readily available and known to one practicing the art. For example, soya bean lecithin is available from Archer Daniels Midland Company in Decatur, Ill. Polyoxythylene stearate, polyoxyethylene sorbitan mono-oleate, polyoxyethylene sorbitan monopalmitate, polyoxyethylene sorbitan monostearate, polyoxyethylene sorbitan monolaurate, citric acid esters of mono and diglycerides of fatty acids, and tartaric acid esters of mono and diglycerides of fatty acids are available from Quest in Owings Mills, Md.

The third component of the fortifier powder of this invention is a source of carbohydrates. Carbohydrate is a major source of readily available energy that the LBW infant needs for growth and that protects the infant from tissue catabolism. In human milk and most standard milk-based infant formulas, the carbohydrate is lactose. LBW infants may be unable to fully digest lactose because lactase activity in the fetal intestine is not fully developed until late in gestation (36 to 40 weeks). On the other hand, sucrose activity is maximal by 32 weeks' gestation, and glucoso-amylase activity, which digests corn syrup solids (glucose polymers), increase twice as rapidly as lactase activity during the third trimester.

As noted above, the carbohydrates will typically be present in an amount of from about 15 wt/wt % to about 75 wt/wt % of the fortifier powder. The preferred carbohydrate level and source is selected to decrease osmolality and viscosity of the reconstituted product. The preferred carbohydrate source is 100% of the carbohydrate component as corn syrup.

The carbohydrates that may be used in the fortifier powder can vary widely. Examples of carbohydrates suitable for preterm infants typically include hydrolyzed cornstarch, maltodextrin, glucose polymers, sucrose, corn syrup, corn syrup solids, rice syrup, glucose, fructose, lactose, high fructose corn syrup and indigestible oligosaccharides such as fructooligosaccharides (FOS). Any single carbohydrate listed above, or any combination thereof, as appropriate may be utilized.

Commercial sources for the carbohydrates listed above are readily available and known to one practicing the art. For example, corn syrup solids are available from Cerestar USA, Inc in Hammond, Ind. Glucose and rice based syrups are available from California Natural Products in Lathrop, Calif. Various corn syrups and high fructose corn syrups are available from Cargil in Minneapolis, Minn. Fructose is available from A. E. Staley in Decatur, Ill. Maltodextrin, glucose polymers, hydrolyzed corn starch are available from American Maize Products in Hammond, Ind. Sucrose is available from Domino Sugar Corp. in New York, N.Y. Lactose is available from Foremost in Baraboo, Wis., and indigestible oligosaccharides such as FOS are available from Golden Technologies Company of Golden, Colo.

The osmolality of the fortified human milk plays an important role in the infant's tolerance of their feedings such as abdominal distention and vomiting/spit-up. Osmolality of the fortified human milk is tied to the level and source of carbohydrate utilized in the fortifier powder. The osmolality of the fortifier powder of the instant invention reconstituted in human milk is typically less than about 400 mOsm/kg water. The substitution of fat for some of the carbohydrate in the fortifier powder of the instant invention serves to reduce the osmolality of fortified human milk by replacing the carbohydrate, which has a high osmotic activity with fat, which has a low osmotic activity. The type of carbohydrate incorporated into the fortifier powder also impacts the osmolality of the fortified human milk. The more hydrolyzed the carbohydrate source (higher DE) the higher the osmotic activity. Additionally, partially hydrolyzed carbohydrate sources may further increase the osmolality when reconstituted with human milk due to further hydrolysis by human milk amylase. Based on the DE values for carbohydrates, one skilled in the art can readily select the carbohydrate source or combination of carbohydrates that will result in the preferred osmolality of the reconstituted fortifier powder/human milk solution.

As stated above, viscosity is also a characteristic of carbohydrates. Viscosity of the reconstituted fortifier powder/human milk solution plays a role in suspending the insoluble minerals during feeding. While higher viscosities tend to reduce insoluble mineral fallout, the higher viscosity can cause tube/nipple clogging. A clogged feeding tube in a continuous feeding apparatus requires additional attention by the nursing staff, who will have to unclog the tube, reset the pump system, which may require a new preparation of fortified human milk. More importantly, a clogged tube prevents the timely delivery of much needed nutrients to a premature infant. The viscosity of the reconstituted fortifier powder/human milk solution of the instant invention is typically less than about 30 cps. Viscosity is inversely related to osmolality. The more hydrolyzed a starch is (higher DE), the lower the viscosity and the higher the osmolality. Based on the DE values for carbohydrates, one skilled in the art can readily select the carbohydrate source or combination of carbohydrates that will drive the viscosity and osmolality characteristics of the reconstituted fortifier powder/human milk solution to the preferred levels.

The fourth component of the fortifier powder of the present invention typically includes supplemented vitamins and minerals.

The preterm infant requires the electrolytes sodium, potassium and chloride for growth and for acid-base balance. Sufficient intakes of these electrolytes are also needed for replacement of losses in the urine and stool and from the skin. Calcium, phosphorus and magnesium are needed for proper bone mineralization. For bones to grow, adequate amounts of these minerals must be present in a feeding. LBW infants may develop rickets or osteopenia if they do not receive adequate amount of calcium and phosphorus in their diet. Phosphorus and magnesium are also found in intracellular fluid. These minerals are needed for the growth and function of soft tissue. Human milk does not provide enough calcium or phosphorus, even if these minerals were to be totally absorbed and retained, which they are not.

Trace minerals are associated with cell division, immune function and growth. Consequently, provision of sufficient amounts of trace minerals is needed for rapid growth in LBW infants. Human milk does not provide sufficient amounts of the trace minerals, especially zinc and copper, to meet the needs of a growing LBW infant. Another trace mineral, iron, is important for the synthesis of hemoglobin, myoglobin and iron-containing enzymes. However, it is not certain that LBW infants need the recommended amounts of iron during the first 2 months of life. The anemia of prematurity occurring shortly after birth cannot be avoided by giving supplemental iron. Also, the preterm infant is estimated to have sufficient iron stores without receiving iron supplementation, if blood loss is small, until 2 months of age. Consequently, the powdered human milk fortifier of the instant invention is low in iron. Zinc is needed for growth, for the activity of numerous enzymes, and for DNA, RNA and protein synthesis. Copper is necessary for the activity of several important enzymes. It is estimated that about 75% of the copper in a term neonate is accumulated during the last 10 to 12 weeks in utero. Consequently, LBW infants, especially those born weighing less than 1500 gm, are likely to have low copper stores. Manganese is needed for the development of bone and cartilage and is important in the synthesis of polysaccharides and glycoproteins.

LBW infants are likely to need more of most vitamins than provided by human milk alone because of low vitamin stores at birth, low intake of feedings, poor absorption of vitamins and clinical conditions requiring increased vitamin intakes.

Vitamin A is a fat-soluble vitamin essential for growth, cell differentiation, vision and the immune system. The vitamin A stores in LBW infants are adequate shortly after birth but decrease soon thereafter. Therefore, preterm infants may require higher intakes of vitamin A than term infants. Vitamin D is important for absorption of calcium and to a lesser extent, phosphorus, and for the development of bone. For many years it was thought that poor bone development observed in LBW infants was due to insufficient vitamin D intake and metabolism and the LBW infants required significantly greater vitamin D intake than term infants. It is now recognized that calcium and phosphorus intakes are more important than vitamin D for bone growth in preterm infants. Vitamin E (tocopherol) prevents peroxidation of polyunsaturated fatty acids in the cell, thus preventing tissue damage. LBW infants may develop hemolytic anemia and vitamin E deficiency when fed feedings low in vitamin E and high in iron and polyunsaturated fatty acids. Additionally, preterm milk contains very low levels of vitamin K.

As are several other water-soluble vitamins, vitamin C is low in mature preterm milk. Folic acid is important in amino acid and nucleotide metabolism. Serum folate concentrations have been shown to fall below normal after 2 weeks of age in LBW infants with low folic acid intakes. Additionally, several B vitamins are present at low concentrations in preterm milk.

The variability of human milk vitamin and mineral concentrations and the increased needs of the preterm infant require a minimal fortification to insure that a developing premature infant is receiving adequate amounts of vitamins and minerals while not over fortifying and possibly causing, for example, hypocalcaemia. Using the recommendations of the FNB, one skilled in the art can readily calculate how much of a vitamin or mineral source should be added to the nutritional product in order to deliver the desired amount of a vitamin or mineral. Practitioners also understand that appropriate additional amounts of vitamin and mineral ingredients need to be provided to nutritional compositions to compensate for some loss during processing and storage of such compositions.

Examples of supplemental vitamins and minerals in the fortifier powder of the instant invention typically include vitamin A, vitamin $B_1$, vitamin $B_2$, vitamin $B_6$, vitamin $B_{12}$, vitamin C, vitamin D, vitamin E, vitamin K, biotin, folic acid, pantothenic acid, niacin, m-inositol, calcium, phosphorus, magnesium, zinc, manganese, copper, sodium, potassium, chloride, iron and selenium. The additional nutrients chromium, molybdenum, iodine, taurine, carnitine and choline may also require supplementation. As discussed above, the fortifier powder will include the natural form of vitamin E in the alpha- to gamma-tocopherol ratio of the instant invention. Preferably, a unit dose typically comprises at least about 25% of the AI for infants for vitamin E.

The nutritional powder of this invention can be manufactured using techniques well known to those skilled in the art. While manufacturing variations are certainly well known to those skilled in the nutritional formulation arts, a few of the manufacturing techniques are described in detail in the Examples. Generally speaking an oil blend is prepared containing all oils, any emulsifier, and the fat soluble vitamins. Two more slurries (carbohydrate and protein) are prepared separately by mixing the carbohydrate and minerals together and the protein in water. The two slurries are then mixed together with the oil blend. The resulting mixture is homogenized, heat processed, standardized with water soluble vitamins, and dried. The resulting powder may be milled to a specific particle size and/or agglomerated to modify particle size and mixability characteristics. Those skilled in the nutritional formulation arts would also be able to dry blend the individual starting materials and add the liquid ingredients through agglomeration or during the dry blending step.

Individual unit dose size packages are preferred over bulk packaging. Because of the small volumes of milk administered to premature infants over the course of a day's feeding, small volumes of fortified human milk are prepared. Powder sterility in a bulk container that has been repeatedly opened, powder scooped out, recovered and stored is always a concern in a hospital environment. Individual unit doses allow for addition of small amounts of powder to human milk without the possibility of contamination of the remaining powder since all of the powder is used in a single preparation. As noted above, the unit dose of the invention typically is the amount of from about 0.5 grams to about 10 grams of fortifier powder in a unit dose. Depending on the volume of a day's feeding, from about 1 to about 4 unit doses will be added to about 25 ml to about 100 ml, respectively.

Numerous types of containers are readily available and known to one practicing the art. Examples of container types typically include packets or sachets, which may be manufactured of paper, foil and plastic film, and foil and plastic film coated paper; and ampoules which may be manufactured of plastic, reinforced paper and glass.

Methods of Use

The methods of the present disclosure include the oral administration of the nutritional compositions, and, in some aspects, infant formulas, disclosed herein to enhance brain development in an individual. The methods include administering to the individual a nutritional composition comprising: i) from about 20 g/L to about 50 g/L of fat; ii) from about 10 g/L to about 15 g/L of protein; wherein said fat comprises RRR alpha-tocopherol and RRR gamma-tocopherol, with a weight ratio of RRR alpha-tocopherol to RRR gamma-tocopherol ranging from about 3.5:1 to about 10:1; and iii) no more than about 8 mg/L of a non-RRR alpha-tocopherol isomer.

In some aspects, the methods include the administration of nutritional compositions having one or more of additional properties (e.g., ingredients and/or concentrations of ingredients) of nutritional compositions disclosed above. Thus, in one aspect, the method involves administering a nutritional composition that has a weight ratio of RRR alpha-tocopherol to RRR gamma-tocopherol of about 5:1. In another aspect, the method involves administering a nutritional composition that is substantially free of non-RRR alpha-tocopherol isomers. In another aspect, the administered nutritional composition includes one or more of a carbohydrate, a polyunsaturated fatty acid, a carotenoid, vitamin C, trans-lutein, and combinations thereof. In a particular aspect, the administered nutritional composition includes a carotenoid. In another aspect, the administered nutritional composition includes a trans-lutein, and, more particularly, all trans-lutein. In another particular aspect, the administered nutritional composition includes vitamin C (e.g., ascorbic acid). In a specific aspect, the administered nutritional composition contains a combination of properties of the above-disclosed nutritional compositions.

In addition to enhancing brain development, the nutritional compositions can be administered to improve cognitive performance, including cognitive development, in an individual, including in an infant or a preterm infant. Particularly, the disclosed combination of RRR-alpha tocopherol, fat, and protein, wherein the presence of non-RRR alpha-tocopherol isomers are limited, including where the administered nutritional composition is substantially free of a non-RRR alpha-tocopherol isomer, may improve general cognition by enhancing memory acquisition, memory retention and memory recall that contributes to the cognitive functions of learning, thinking, and memory.

The nutritional compositions as described herein can be administered to individuals including infants generally, or may, in some embodiments, be administered to a specific subclass of infants that are "in need thereof;" that is, to specific infants that would specifically benefit by administration of the infant formula. For example, a specific infant may be "in need of" the infant formulas as described herein if they are susceptible to (i.e., genetically predisposed, have a family history of, and/or having symptoms of the disease or condition) neurodegenerative diseases or other diseases and conditions that can impair/reduce cognition generally or specific aspects of cognition. In certain embodiments of the methods, the individual is a preterm infant.

The individual desirably consumes at least one serving of the nutritional composition daily, and in some embodiments, may consume two, three, or even more servings per day. In certain embodiments of the methods, the nutritional composition is an infant formula. In certain embodiments of the methods, the nutritional composition is a preterm infant formula. Each serving is desirably administered as a single, undivided dose, although the serving may also be divided into two or more partial or divided servings to be taken at two or more times during the day. The methods of the present disclosure include continuous day after day administration, as well as periodic or limited administration, although continuous day after day administration is generally desirable. The methods of the present disclosure are preferably applied on a daily basis, wherein the daily administration is maintained continuously for at least 3 days, including at least 5 days, including at least 1 month, including at least 6 weeks, including at least 8 weeks, including at least 2 months, including at least 6 months, desirably for at least about 18-24 months, desirably as a long term, continuous, daily, dietary source or supplement.

EXAMPLE 1

As discussed above, the alpha- to gamma-tocopherol ratio of this invention may be incorporated into infant nutritional formulas.

A batch of powder infant formula is manufactured as described in Example II except that the processed mix is sent to a spray dryer as described below.

The processed mix is preheated through a plate heater to 71° C.-82° C. before going to a surge tank. The mix leaves the surge tank and passes through the steam injector where it is heated to 88° C.-93° C. The mix enters the vapor-flash chamber where it is cooled to 71° C.-82° C., then pumped through an in-line 200 micro filter prior to the high-pressure pump and into the dryer. The dryer settings are as follows: the nozzle pressure 3000-5000 psig, the liquid flow rate 11 gpm max, the ingoing air temperature 160° C.-207° C., and outgoing air temperature 82° C.-108° C.

To control bulk density, dispensability, particle size, moisture and physical stability, the specific spray nozzle, nozzle pressure, drying temperatures and fine reinjection parameters may vary depending upon the drying conditions of the day. The powder passes from the dryer into the powder cooler where the powder is cooled to below 43° C. The cooled powder is stored in appropriate containers until being filled into the desired packaging.

EXAMPLE II

As discussed above, the alpha- to gamma-tocopherol ratio of this invention may be incorporated into a human milk fortifier powder, which is added to human milk.

A batch of fortifier powder is manufactured by combining the appropriate ingredients to generate one carbohydrate/mineral (CHO/MIN) slurry, one oil blend and one protein in water (PIW) slurry. The CHO/MIN, oil blend and PIW slurries are mixed together to form the final blend. The final blend is then processed with an HTST treatment. After standardization, the final blend is spray dried.

Table 5 presents a bill of materials for manufacturing 8,172 kg of powdered human milk fortifier. A detailed description of its manufacture follows.

TABLE 5

Bill of Materials

| Ingredient | Amount |
| --- | --- |
| Ingredient water | 16,205 L |
| Corn syrup solids | 1603 kg |
| Magnesium chloride | 96.2 kg |
| Potassium citrate | 223.8 kg |
| Sodium citrate | 6.6 kg |
| Sodium chloride | 15.4 kg |
| MCT oil | 801 kg |
| Lecithin | 16.6 kg |
| Vitamin A | 2.36 kg |
| Vitamin D | 359.3 g |
| Vitamin K | 27.5 g |
| RRR alpha-tocopherol acetate | 13.2 kg |
| RRR gamma-tocopherol acetate | 2.6 kg |
| Calcium carbonate | 33.1 kg |
| Tricalcium phosphate | 646 kg |
| Whey protein concentrate | 1506 kg |
| Non fat dry milk | 3307 kg |
| Potassium citrate | 257.2 g |
| Ferrous sulfate | 3.7 kg |
| Zinc sulfate | 11.1 kg |
| Copper sulfate | 1.84 kg |
| Manganese sulfate | 0.320 kg |
| Sodium selenate | 0.001 kg |
| Niacinamide | 0.98 k |
| Riboflavin | 1.14 kg |
| Calcium pantothenate | 4.08 kg |
| Pyridoxine hydrochloride | 0.655 kg |
| m-inositol | 9.55 kg |
| Biotin | 0.0727 kg |
| Folic acid | 0.0775 kg |
| Cyanocobalamin | 0.0016 kg |
| Ascorbic acid | 153.5 kg |

A carbohydrate/mineral slurry is prepared by heating 2,763 liters of ingredient water to 54° C.-62° C. With agitation, the specified amounts of corn syrup solids (Maltrin M200 distributed by Grain Processing Corporation, Muscatine, Iowa), magnesium chloride, sodium chloride, sodium citrate, potassium citrate, ultra micronized tricalcium phosphate and calcium carbonate are added to the heated water. The slurry is held under agitation at 54° C.-62° C. for not longer than six hours until it is blended with the other slurries.

An oil blend is prepared by heating the specified amount of oil (distributed by Stepan, Maywood, N.J.) to 32° C.-37° C. with agitation. An emulsifier (standard fluid lecithin distributed by Central Soya, Ft. Wayne, Ind.) is then added under agitation and allowed to dissolve. Vitamin A, D, K and Vitamin E (distributed by Vitamins, Inc., Chicago, Ill.) are then added to the slurry with agitation. The completed oil slurry is held under moderate agitation at a temperature from 26° C. to 48° C. for a period of no longer than six hours until it is blended with the other slurries.

A protein-in-water slurry is prepared by heating 9,053 liters of ingredient water to 48° C.-60° C. With agitation, the specified amount of whey protein concentrate (AMP 800 distributed by AMPC, Inc. Ames, Iowa) and nonfat dry milk is added to the heated water. The completed protein-in-water slurry is not held but blended directly with the other slurries.

The protein-in-water, oil blend and carbohydrate/mineral slurries are blended together with agitation and the resultant blend is maintained at a temperature from 51° C. to 60° C. After waiting for at least five minutes with agitation the final blend pH is adjusted with 1N KOH to a pH from 6.45 to 6.80. The total solids of the final blend is 30%. The final blend is held for no longer than two hours after the pH check.

After waiting for a period of not less than five minutes nor greater than two hours, the blend is subjected to deaeration, high-temperature-short-time heat treatment, and homogenization, as follows: deaerate the blend at 10-15 inches Hg; emulsify the blend at 900-1100 psig in a single stage homogenizer; pass the blend through a plate/coil heater and heat the mix to 71° C. to 82° C.; homogenize the blend at 3900 to 4100/400 to 600 psig in a double stage homogenizer; pass the blend through a 16 second hold tube at a temperature from 73° C. to 85° C.; cool the blend to a temperature from 1° C. to 7° C.; and store the blend at a temperature from 1° C. to 7° C.

After the above steps have been completed, appropriate analytical testing for quality control is conducted. Based on the analytical results of the quality control tests, batch corrections are made if need be. Final blend total solids are from 29% to 31%.

A water soluble vitamin solution, ascorbic acid solution and trace mineral solution are prepared separately and added to the processed blend.

The ascorbic acid solution is prepared by adding the required amount of ascorbic acid to 2,453 liters of 10° C. to 37° C. water with agitation.

The mineral solution is prepared by heating 321 liters of ingredient water to 37° C. to 65° C. Under agitation, add the required amount of potassium citrate and ferrous sulfate. Allow to agitate until the solution is a clear green color. Add the required amounts of zinc sulfate, copper sulfate, manganese sulfate and sodium selenate to the green mineral solution. Agitate five minutes minimum.

The water soluble vitamin solution is prepared by heating 530 liters of ingredient water to 37° C. to 65° C. The required quantities of niacinamide, riboflavin, calcium pantothenate, pyridoxine hydrochloride, thiamine hydrochloride, m-inositol, biotin, folic acid and cyanocobalamin are added to the heated water.

All of the ascorbic acid solution, the mineral solution and water soluble vitamin solution is then added to the blended slurry under agitation.

The final mix is preheated through a plate heater to 71° C.-82° C. before going to a surge tank. The mix leaves the surge tank and passes through the steam injector where it is heated to 88° C.-93° C. The mix enters the vapor-flash chamber where it is cooled to 71° C.-82° C., then pumped through an in-line 200 micro filter prior to the high pressure pump and into the dryer. The dryer settings are as follows: the nozzle pressure of 3000-5000 psig, the liquid flow rate at 11 gpm max, the in-going air temperature at 160° C.-207° C., and the out-going air temperature at 82° C.-108° C.

To control bulk density, dispensability, particle size, moisture and physical stability, the specific spray nozzle, nozzle pressure, drying temperatures and fine reinjection parameters may vary depending upon the drying conditions of the day. The powder passes from the dryer into the powder cooler where the powder is cooled to below 43° C. The cooled powder is stored in appropriate containers until being filled in individual packets.

What is claimed is:

1. A nutritional composition comprising fat, protein, carbohydrates, minerals and from about 5 mg/L to about 100 mg/L of an optimized tocopherol blend having a weight ratio of RRR alpha-tocopherol to RRR gamma-tocopherol of from 4:1 to about 20:1 and less than about 8 mg/L of non-RRR alpha-tocopherol isomer.

2. The nutritional composition of claim 1, wherein the nutritional composition comprises less than about 5 mg/L of non-RRR alpha-tocopherol isomer.

3. The nutritional composition of claim 1, wherein the nutritional composition comprises less than about 0.5 mg/L of non-RRR alpha-tocopherol isomer.

4. The nutritional composition of claim 1, wherein the nutritional composition is substantially free of non-RRR alpha-tocopherol isomer.

5. The nutritional composition of claim 1, wherein the weight ratio of RRR alpha-tocopherol to RRR gamma-tocopherol ranges from 4:1 to about 15:1.

6. The nutritional composition of claim 1, wherein the weight ratio of RRR alpha-tocopherol to RRR gamma-tocopherol ranges from 4:1 to about 10:1.

7. The nutritional composition of claim 1, wherein the weight ratio of RRR alpha-tocopherol to RRR gamma-tocopherol is about 5:1.

8. The nutritional composition of claim 1, having: (i) from about 20 to about 50 g/L fat; ii) from about 10 to about 15 g/L protein; and iii) at least about 4 mg/L of RRR alpha-tocopherol.

9. The nutritional composition of claim 1, wherein the nutritional composition comprises a polyunsaturated fatty acid selected from arachidonic acid, docosahexaenoic acid, and a combination thereof.

10. The nutritional composition of claim 1, wherein the nutritional composition comprises vitamin C.

11. The nutritional composition of claim 1, wherein the nutritional composition comprises a carotenoid.

12. The nutritional composition of claim 1, wherein the nutritional composition comprises trans-lutein.

13. The nutritional composition of claim 1, wherein the nutritional composition is a liquid nutritional product.

14. The nutritional composition of claim 1, wherein the nutritional composition is a powdered nutritional product.

15. The nutritional composition of claim 1, wherein the nutritional composition is an infant formula.

16. The nutritional composition of claim 1, wherein the nutritional composition is a preterm infant formula.

* * * * *